United States Patent
Plotkin et al.

(10) Patent No.: US 10,519,264 B2
(45) Date of Patent: *Dec. 31, 2019

(54) POLYMER PARTICLES

(71) Applicant: Terumo Corporation, Tokyo (JP)

(72) Inventors: Steve Plotkin, Tustin, CA (US); Gregory M. Cruise, Rancho Santa Margarita, CA (US); Edward Michael Keeley, Huntington Beach, CA (US); Renee Yu, Tustin, CA (US); Clayton Harris, Irvine, CA (US)

(73) Assignee: Terumo Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/147,225

(22) Filed: Sep. 28, 2018

(65) Prior Publication Data
US 2019/0031798 A1 Jan. 31, 2019

Related U.S. Application Data

(63) Continuation of application No. 15/604,529, filed on May 24, 2017, now Pat. No. 10,118,980, which is a (Continued)

(51) Int. Cl.
*A61L 24/00* (2006.01)
*A61L 31/04* (2006.01)
(Continued)

(52) U.S. Cl.
CPC .......... *C08F 220/28* (2013.01); *A61K 9/0019* (2013.01); *A61K 9/146* (2013.01);
(Continued)

(58) Field of Classification Search
CPC .... C08F 220/28; C08F 220/10; C08F 220/38; C08F 290/062; C08G 65/33324;
(Continued)

(56) References Cited

U.S. PATENT DOCUMENTS 4,070,348 A 1/1978 Kraemer et al.
4,157,323 A 6/1979 Yen et al.
(Continued)

FOREIGN PATENT DOCUMENTS

CN 103709323 A 4/2014
EP 0240424 B1 5/1991
(Continued)

OTHER PUBLICATIONS

Blinova et al., Poly(ethylene glycol) containing functionalized polymer membranes for carbon dioxide separation. Preprints-American Chemical Society, Division of Energy & Fuels, 59(1):433-434 (2014).
(Continued)

*Primary Examiner* — Alexandre F Ferre
(74) *Attorney, Agent, or Firm* — K&L Gates LLP; Louis C. Cullman; Brian J. Novak (57) ABSTRACT

Polymer particle embolics and methods of making same are described. The particle embolics can be used as embolization agents.

20 Claims, 3 Drawing Sheets

Related U.S. Application Data continuation of application No. 14/536,394, filed on Nov. 7, 2014, now Pat. No. 9,688,788.

(60) Provisional application No. 61/902,020, filed on Nov. 8, 2013.

(51) Int. Cl.

| | |
|---|---|
| *A61L 31/14* | (2006.01) |
| *C08F 236/20* | (2006.01) |
| *A61L 24/06* | (2006.01) |
| *A61K 31/4745* | (2006.01) |
| *A61K 31/555* | (2006.01) |
| *A61L 26/00* | (2006.01) |
| *A61K 47/69* | (2017.01) |
| *C08F 220/56* | (2006.01) |
| *C08F 220/28* | (2006.01) |
| *C08F 22/38* | (2006.01) |
| *A61K 9/14* | (2006.01) |
| *A61K 31/704* | (2006.01) |
| *A61K 9/00* | (2006.01) |
| *A61K 9/50* | (2006.01) |
| *C08F 290/06* | (2006.01) |
| *A61K 47/32* | (2006.01) |
| *C08F 220/38* | (2006.01) |
| *C08G 65/333* | (2006.01) |
| *C08F 220/10* | (2006.01) |

(52) U.S. Cl.
CPC .......... *A61K 9/5026* (2013.01); *A61K 31/704* (2013.01); *A61K 47/32* (2013.01); *A61L 24/0015* (2013.01); *A61L 24/06* (2013.01); *C08F 22/385* (2013.01); *C08F 220/10* (2013.01); *C08F 220/38* (2013.01); *C08F 290/062* (2013.01); *C08G 65/33324* (2013.01); *A61L 2300/418* (2013.01); *C08F 2220/282* (2013.01); *C08F 2220/382* (2013.01); *Y10T 428/2982* (2015.01)

(58) Field of Classification Search
CPC .... A61K 9/0019; A61K 9/146; A61K 9/5026; A61K 31/704; A61K 47/32; A61L 24/0015; A61L 24/06
USPC .......................................................... 428/402
See application file for complete search history.

(56) References Cited

U.S. PATENT DOCUMENTS

| | | |
|---|---|---|
| 4,925,677 A | 5/1990 | Feijen |
| 5,417,982 A | 5/1995 | Modi |
| 5,545,423 A | 8/1996 | Soon-Shiong et al. |
| 5,635,215 A | 6/1997 | Boschetti et al. |
| 5,648,100 A | 7/1997 | Boschetti et al. |
| 5,662,935 A | 9/1997 | Motta |
| 5,759,578 A | 6/1998 | Soon-Shiong et al. |
| 5,879,709 A | 3/1999 | Soon-Shiong et al. |
| 5,906,997 A | 5/1999 | Schwartz et al. |
| 5,922,357 A | 7/1999 | Coombes et al. |
| 6,087,450 A | 7/2000 | Breitbach et al. |
| 6,218,440 B1 | 4/2001 | Kitagawa |
| 6,248,363 B1 | 6/2001 | Yoshikawa et al. |
| 6,306,922 B1 | 10/2001 | Hubbell et al. |
| 6,309,669 B1 | 10/2001 | Setterstrom et al. |
| 6,403,569 B1 | 6/2002 | Achterrath |
| 6,548,081 B2 | 4/2003 | Sadozai et al. |
| 6,555,138 B1 | 4/2003 | Karlsson et al. |
| 6,569,463 B2 | 5/2003 | Patel |
| 6,689,374 B2 | 2/2004 | Chu et al. |
| 6,790,456 B2 | 9/2004 | Vogel et al. |
| 6,794,370 B2 | 9/2004 | Achterrath |
| 6,923,988 B2 | 8/2005 | Patel |
| 6,946,146 B2 | 9/2005 | Muyle |
| 7,070,809 B2 | 7/2006 | Goupil et al. |
| 7,094,369 B2 | 8/2006 | Buiser et al. |
| 7,144,588 B2 | 12/2006 | Oray et al. |
| 7,153,572 B2 | 12/2006 | Cooper et al. |
| 7,442,385 B2 | 10/2008 | Lewis et al. |
| 7,449,236 B2 | 11/2008 | Lanphere et al. |
| 7,462,366 B2 | 12/2008 | Lanphere et al. |
| 7,588,780 B2 | 9/2009 | Buiser et al. |
| 7,591,993 B2 | 9/2009 | Boschetti |
| 7,670,592 B2 | 3/2010 | Boschetti |
| 7,736,671 B2 | 6/2010 | DiCarlo et al. |
| 7,776,240 B2 | 8/2010 | Chu et al. |
| 7,794,755 B2 | 9/2010 | Figuly et al. |
| 7,838,035 B2 | 11/2010 | Figuly |
| 7,838,699 B2 | 11/2010 | Schwarz et al. |
| 7,842,377 B2 | 11/2010 | Lanphere et al. |
| 7,858,119 B1 | 12/2010 | Odidi et al. |
| 7,887,846 B2 | 2/2011 | Figuly |
| 7,897,179 B2 | 3/2011 | Muyle |
| 7,951,402 B2 | 5/2011 | Lanphere et al. |
| 8,062,673 B2 | 11/2011 | Figuly et al. |
| 8,110,226 B2 | 2/2012 | Li |
| 8,143,042 B2 | 3/2012 | Bettinger et al. |
| 8,182,807 B2 | 5/2012 | Labhasetwar et al. |
| 8,201,689 B2 | 6/2012 | Kaem |
| 8,226,926 B2 | 7/2012 | Reb |
| 8,252,302 B2 | 8/2012 | Macdonald |
| 8,323,698 B2 | 12/2012 | Gu et al. |
| 8,323,794 B2 | 12/2012 | Chu et al. |
| 8,329,224 B2 | 12/2012 | Hall et al. |
| 8,367,099 B2 | 2/2013 | Herweck et al. |
| 8,383,758 B2 | 2/2013 | Papisov |
| 8,426,481 B2 | 4/2013 | Hassleholm et al. |
| 8,617,132 B2 | 12/2013 | Golzarian et al. |
| 8,673,266 B2 | 3/2014 | Boschetti |
| 8,691,791 B2 | 4/2014 | Lewis et al. |
| 8,697,137 B2 | 4/2014 | Vogel et al. |
| 8,709,384 B2 | 4/2014 | Reb |
| 8,739,978 B2 | 6/2014 | Yoon et al. |
| 8,741,351 B2 | 6/2014 | Vogel et al. |
| 9,688,788 B2 * | 6/2017 | Plotkin .................. A61K 9/146 |
| 9,938,367 B2 | 4/2018 | Cruise et al. |
| 10,118,980 B1 * | 11/2018 | Plotkin .................. A61K 9/146 |
| 10,144,793 B2 | 12/2018 | Cruise et al. |
| 10,155,064 B2 | 12/2018 | Cruise et al. |
| 2002/0028243 A1 | 3/2002 | Masters |
| 2002/0068089 A1 | 6/2002 | Vogel et al. |
| 2002/0071855 A1 | 6/2002 | Sadozai et al. |
| 2002/0197326 A1 | 12/2002 | Vogel et al. |
| 2003/0078339 A1 | 4/2003 | Kiser et al. |
| 2003/0183962 A1 | 10/2003 | Buiser et al. |
| 2003/0206864 A1 | 11/2003 | Mangin |
| 2004/0161466 A1 | 8/2004 | Lewis et al. |
| 2005/0196702 A1 | 9/2005 | Bryant et al. |
| 2005/0267556 A1 | 12/2005 | Shuros et al. |
| 2006/0025560 A1 | 2/2006 | Inoue et al. |
| 2006/0069168 A1 | 3/2006 | Tabata et al. |
| 2006/0222596 A1 | 10/2006 | Askari et al. |
| 2006/0240435 A1 | 10/2006 | Minoura et al. |
| 2006/0251582 A1 | 11/2006 | Reb |
| 2007/0035296 A1 | 2/2007 | Potapov et al. |
| 2007/0213683 A1 | 9/2007 | Cassingham et al. |
| 2007/0237741 A1 | 10/2007 | Figuly et al. |
| 2007/0237742 A1 | 10/2007 | Figuly et al. |
| 2007/0237830 A1 | 10/2007 | Figuly |
| 2007/0237956 A1 | 10/2007 | Figuly et al. |
| 2008/0033366 A1 | 2/2008 | Matson et al. |
| 2008/0039890 A1 | 2/2008 | Matson et al. |
| 2008/0102029 A1 | 5/2008 | Fritz et al. |
| 2008/0113029 A1 | 5/2008 | Fritz et al. |
| 2008/0220077 A1 | 9/2008 | Vogel et al. |
| 2009/0029077 A1 | 1/2009 | Atanasoska et al. |
| 2009/0092677 A1 | 4/2009 | Richard |
| 2009/0117033 A1 | 5/2009 | O'Gara |
| 2009/0164013 A1 | 6/2009 | Cruise et al. |
| 2009/0246275 A1 | 10/2009 | O'Gara et al. |
| 2009/0253809 A1 | 10/2009 | Gomurashvili et al. |

(56) References Cited

U.S. PATENT DOCUMENTS

| | | |
|---|---|---|
| 2010/0028260 A1 | 2/2010 | Fritz et al. |
| 2010/0040688 A1 | 2/2010 | Elbert et al. |
| 2010/0057027 A1 | 3/2010 | Furno et al. |
| 2010/0166876 A1 | 7/2010 | Lewis et al. |
| 2010/0247667 A1 | 9/2010 | Ariga et al. |
| 2010/0261646 A1 | 10/2010 | Lavik et al. |
| 2011/0009327 A1 | 1/2011 | Hill et al. |
| 2011/0009520 A1 | 1/2011 | Figuly et al. |
| 2011/0033548 A1 | 2/2011 | Lai et al. |
| 2011/0033608 A1 | 2/2011 | Figuly et al. |
| 2011/0038936 A1 | 2/2011 | Griswold et al. |
| 2011/0082427 A1 | 4/2011 | Golzarian et al. |
| 2011/0091550 A1 | 4/2011 | Zhang et al. |
| 2011/0152765 A1 | 6/2011 | Weber et al. |
| 2011/0182998 A1 | 7/2011 | Reb et al. |
| 2011/0212179 A1 | 9/2011 | Liu |
| 2012/0129798 A1 | 5/2012 | Akala et al. |
| 2012/0135170 A1 | 5/2012 | Meldal et al. |
| 2012/0213831 A1 | 8/2012 | Vogel et al. |
| 2012/0276151 A1 | 11/2012 | Lewis et al. |
| 2012/0289995 A1 | 11/2012 | Constant et al. |
| 2012/0302654 A1 | 11/2012 | Cruise et al. |
| 2013/0052142 A1 | 2/2013 | Harder et al. |
| 2013/0190795 A1 | 7/2013 | Matson et al. |
| 2013/0315838 A1 | 11/2013 | Reb et al. |
| 2013/0323306 A1 | 12/2013 | Weber |
| 2014/0162969 A1 | 6/2014 | Lewis et al. |
| 2014/0186601 A1 | 7/2014 | Chang et al. |
| 2015/0079328 A1 | 3/2015 | Cruise et al. |
| 2015/0079395 A1 | 3/2015 | Cruise et al. |
| 2015/0166696 A1 | 6/2015 | Plotkin et al. |
| 2015/0306227 A1 | 10/2015 | Cruise et al. |
| 2016/0279282 A1 | 9/2016 | Cruise et al. |
| 2016/0311990 A1 | 10/2016 | Cruise et al. |
| 2017/0081450 A1 | 3/2017 | Cruise et al. |
| 2018/0085487 A1 | 3/2018 | Cruise et al. |
| 2018/0085497 A1 | 3/2018 | Hincapie et al. |
| 2019/0062479 A1 | 2/2019 | Cruise et al. |
| 2019/0076571 A1 | 3/2019 | Cruise et al. |
| 2019/0134257 A1 | 5/2019 | Hincapie et al. |

FOREIGN PATENT DOCUMENTS

| | | |
|---|---|---|
| EP | 1534351 B1 | 10/2006 |
| EP | 1820495 A2 | 8/2007 |
| EP | 1267839 B1 | 10/2007 |
| EP | 2269580 A2 | 1/2011 |
| EP | 1796644 B1 | 4/2011 |
| EP | 1986706 B1 | 8/2011 |
| EP | 2368581 A2 | 9/2011 |
| EP | 2475695 B1 | 4/2014 |
| EP | 2286799 B1 | 7/2015 |
| JP | H05-279416 A | 10/1993 |
| JP | 2003-245544 A | 9/2003 |
| JP | 2011-201031 A | 10/2011 |
| JP | 2011-245267 A | 12/2011 |
| JP | 2012-170773 A | 9/2012 |
| JP | 2012-187308 A | 10/2012 |
| JP | 2014-218439 A | 11/2014 |
| WO | 1995/019186 A2 | 7/1995 |
| WO | 2001/072281 A2 | 10/2001 |
| WO | 2002/015913 A1 | 2/2002 |
| WO | 2002/071994 A1 | 9/2002 |
| WO | 2003/094930 A1 | 11/2003 |
| WO | 2006/081517 A2 | 8/2006 |
| WO | 2006/119968 A2 | 11/2006 |
| WO | 2007/035296 A2 | 3/2007 |
| WO | 2007/133020 A1 | 11/2007 |
| WO | 2008/034911 A1 | 3/2008 |
| WO | 2008/047095 A1 | 4/2008 |
| WO | 2008/057163 A2 | 5/2008 |
| WO | 2008/128580 A1 | 10/2008 |
| WO | 2008/136536 A1 | 11/2008 |
| WO | 2009/015281 A2 | 1/2009 |
| WO | 2009/040434 A1 | 4/2009 |
| WO | 2009/073193 A2 | 6/2009 |
| WO | 2009/130332 A1 | 10/2009 |
| WO | 2009/131982 A1 | 10/2009 |
| WO | 2010/063630 A2 | 6/2010 |
| WO | 2011/014722 A2 | 2/2011 |
| WO | 2011/029867 A1 | 3/2011 |
| WO | 2011/068455 A1 | 6/2011 |
| WO | 2012/073188 A1 | 6/2012 |
| WO | 2012/120138 A1 | 9/2012 |
| WO | 2012/121073 A1 | 9/2012 |
| WO | 2012/133737 A1 | 10/2012 |
| WO | 2012/145431 A2 | 10/2012 |
| WO | 2012/166594 A1 | 12/2012 |
| WO | 2013/130143 A2 | 9/2013 |
| WO | 2013/177364 A1 | 11/2013 |
| WO | 2014/034787 A1 | 3/2014 |
| WO | 2015/042461 A1 | 3/2015 |
| WO | 2015/042462 A1 | 3/2015 |
| WO | 2015/070094 A1 | 5/2015 |
| WO | 2016/154592 A1 | 9/2016 |
| WO | 2018/064389 A1 | 4/2018 |
| WO | 2018/064390 A1 | 4/2018 |

OTHER PUBLICATIONS

International Search Report and Written Opinion dated Dec. 24, 2014 for International Application No. PCT/US2014/056647 filed on Sep. 19, 2014.

International Search Report and Written Opinion dated Feb. 27, 2015 for International Application No. PCT/US2014/064680 filed on Nov. 7, 2014.

International Search Report and Written Opinion dated Dec. 24, 2014 for International Application No. PCT/US2014/056644 filed on Sep. 19, 2014.

Kamitani et al., Design of cell-surface-retained polymers for artificial ligand display. ChemBioChem, 10(2):230-233 (2009).

Supplementary European Search Report dated Apr. 19, 2017 for European Application No. 14845609.

Supplementary European Search Report dated Apr. 6, 2017 for European Application No. 14845676.7.

International Search Report and Written Opinion dated Jun. 2, 2016 for International Application No. PCT/US2016/024340 filed on Mar. 25, 2016.

Tarasyuk et al., Investigation into the influence of organic modifiers and ultradispersed hybrid fillers on the structure and properties of glass-ceramic coatings prepared by the sol-gel method. Glass Physics and Chemistry, vol. 32, No. 4, pp. 439-447 (2006).

European Search Report and Search Opinion dated Jul. 10, 2017 for European Patent Application Serial No. 14859554.9.

International Search Report and Written Opinion dated Dec. 20, 2017 for International Application No. PCT/US2017/054118 filed on Sep. 28, 2017.

International Search Report and Written Opinion dated Feb. 27, 2018 for International Application No. PCT/US2017/054113 filed on Sep. 28, 2017.

U.S. Appl. No. 16/258,313, filed Jan. 25, 2019.

U.S. Appl. No. 16/403,364, filed May 3, 2019.

* cited by examiner

POLYMER PARTICLES

CROSS REFERENCE TO RELATED APPLICATIONS

This application is a continuation of U.S. patent application Ser. No. 15/604,529, filed May 24, 2017, which continuation of U.S. patent application Ser. No. 14/536,394, filed Nov. 7, 2014, now U.S. Pat. No. 9,688,788, which claims the benefit of U.S. Provisional Patent Application No. 61/902,020, filed Nov. 8, 2013, the entire disclosure each of which is incorporated herein by reference.

FIELD

Polymer particles for the occlusion of vascular sites and cavities within the body, such as the embolization of vascularized tumors or arteriovenous malformations are described.

SUMMARY

Described herein generally are particles including a polyether and optionally one or more monomers. These polymers can be used for/in embolization. The polymer particles are compressible for ease of delivery. Further, in some embodiments, the polymer particles are stable in/at physiological conditions. In some embodiments, the particles can be loaded or coated with a drug(s) or active agent(s).

Polymer particles as described can comprise: at least one polyether including at least two functional groups and optionally at least one monomer. Particles as described herein can have various sizes depending on a particular use, but generally can have diameters less than about 1,200 μm.

Further, in other embodiments, polymer particles are described comprising: at least one derivatized poly(ethylene glycol) macromer, poly(propylene glycol) macromer, poly(tetramethylene oxide) macromer, or a combination thereof at a concentration of between about 15% w/w and about 50% w/w; and at least one monomer that is not n-isopropyl acrylamide.

The polymer particles can have an average diameter between about 40 μm and about 1,200 μm.

The polymer particles can further include at least one monomer. The at least one monomer can include a functional group. The functional group can be an acrylate, acrylamide, methacrylate, or methacrylamide. Further, the at least one monomer can be glycerol monomethacrylate, amino ethyl methacrylate, 3-sulfopropyl acrylate, amino propyl methacrylate, or a combination thereof.

In one embodiment, the at least one monomer is glycerol monomethacrylate at a concentration of about 68% w/w. In another embodiment, the at least one monomer is 3-sulfopropyl acrylate at a concentration of about 59% w/w. In still another embodiment, the at least one monomer is amino propyl methacrylate at a concentration of about 1% w/w. In yet another embodiment, the at least one monomer is amino ethyl methacrylate at a concentration of about 3% w/w.

In some embodiments, the at least one derivatized poly(ethylene glycol) macromer can be poly(ethylene glycol) diacrylamide, poly(ethylene glycol) diacrylate, poly(ethylene glycol) dimethacrylate, poly(ethylene glycol) dimethacrylamide, or a combination thereof.

Methods of making polymer particles as described herein are also disclosed. These methods can comprise: reacting an aqueous based prepolymer solution including at least one derivatized polyether macromer and an initiator in an oil to form polymer particles; wherein said polymer particle has a diameter less than about 1,200 μm.

In some embodiments of the methods, the oil is a mineral oil. In other embodiments of the methods, the initiator is ammonium persulfate, tetramethylethylene diamine, or a combination thereof.

In embodiments of the methods and particles described herein, the compositions and particles do not include n-isopropyl acrylamide.

DETAILED DESCRIPTION

Described herein generally are particles made of polymer material including a reaction product of at least one polyether macromer, optionally at least one monomer, optionally at least one multifunctional crosslinker, and optionally at least one initiator. The particles can be referred to herein as being microparticles, microspheres, microbeads, spheres, microembolis, embolics, and the like. The particles can have diameters less than about 1,200 μm. The particles can also be compressible, biostable, and/or durable for ease of delivery.

The particles can be formed from a prepolymer solution or mixture comprising: (i) one or more polyether macromers that contain at least two functional groups amenable to polymerization, (ii) optionally one or more monomers, and (iii) optionally one or more multifunctional crosslinkers. In some embodiments, a polymerization initiator may be utilized.

In one embodiment, the macromer includes a plurality of functional groups suitable or amenable to polymerization. In some embodiments, the macromer can be linear. In other embodiments, the macromer can have one or more branches. In still other embodiments, the macromer can be an ethylenically unsaturated macromer. Macromers can include polyethers. Polyether macromers can include linear or branched poly(ethylene glycol), poly(propylene glycol), poly(tetramethylene oxide), derivatives thereof, or combinations thereof.

Macromers described herein can have molecular weights of about 200 grams/mole, 400 grams/mole, 600 grams/mole, 800 grams/mole, 1,000 grams/mole, 2,000 grams/mole, 3,000 grams/mole, 4,000 grams/mole, 5,000 grams/mole, 10,000 grams/mole, 15,000 grams/mole, 20,000 grams/mole, 25,000 grams/mole, 30,000 grams/mole, 35,000 grams/mole, between about 200 grams/mole and about 35,000 grams/mole, between about 200 grams/mole and about 30,000 grams/mole, between about 1,000 grams/mole and about 15,000 grams/mole, at least about 200 grams/mole, at most about 30,000 g/mole, or at most about 35,000 grams/mole. In one embodiment, macromers can have a molecular weight of about 10,000 g/mole.

Derivatives of these polyethers can be prepared to render them amenable to polymerization. While any type of chemistry can be utilized, for example nucleophile/N-hydroxysuccinimde esters, nucleophile/halide, vinyl sulfone/acrylate or maleimide/acrylate; a preferred chemistry is free radical polymerization. As such, polyethers with a plurality of ethylenically unsaturated groups, such as acrylate, acrylamide, methacrylate, methacrylamide, and vinyl, can be used. In one embodiment, a polyether macromer can be poly(ethylene glycol) diacrylamide with a molecular weight of about 10,000 g/mole.

In another embodiment the macromer is poly(ethylene glycol) diacrylamide, poly(ethylene glycol) diacrylate, poly(ethylene glycol) dimethacrylate, poly(ethylene glycol) dimethacrylamide, derivatives thereof, or combinations thereof.

Macromers can be included at a concentration in the solution of about 0% w/w, about 1% w/w, about 2% w/w, about 3% w/w, about 4% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 35% w/w, about 30% w/w, about 35% w/w, about 40% w/w, about 45% w/w, about 50% w/w, about 60% w/w, about 70% w/w, between about 5% w/w and about 10% w/w, between about 5% w/w and about 20% w/w, between about 5% w/w and about 25% w/w, between about 5% w/w and about 15% w/w, between about 6% w/w and about 8% w/w, or between about 14% w/w and about 16% w/w. In some embodiments, a macromer need not be used.

In one embodiment, the macromer can be included at a concentration of about 7% w/w in the solution.

In one embodiment, the macromer can be included at a concentration of about 15% w/w in the solution.

In some embodiments, if one of the monomer(s) and/or macromers(s) is a solid, a solvent can be used to form a solution from which the particles for use as embolics can be prepared. If liquid monomers and macromers are utilized, a solvent may not be required. In some embodiments, even when using liquid monomers and/or macromers, a solvent may still be used. Solvents may include any liquid that can dissolve or substantially dissolve a polyether macromer, monomers, multifunctional crosslinkers, and/or initiators. Any aqueous or organic solvent may be used that dissolves the desired monomer(s), macromer(s), multifunctional crosslinker(s) and/or polymerization initiators. In one embodiment, the solvent can be water. Additionally, solutes, e.g. sodium chloride, may be added to the solvent to increase the rate of polymerization. Solvent concentration can be varied to alter the compressibility of the embolic particle, allowing for delivery through a catheter of smaller inner diameter than the diameter of the particle.

Solvent concentrations can be about 25% w/w, about 35% w/w, about 45% w/w, about 55% w/w, about 65% w/w, about 75% w/w, about 85% w/w, about 95% w/w, between about 40% w/w and about 80% w/w, between about 30% w/w and about 90% w/w, or between about 50% w/w and about 70% w/w of the solution. In one embodiment, the solvent concentration can be about 50% w/w, about 51% w/w, about 52% w/w, about 53% w/w, about 54% w/w, about 55% w/w, about 56% w/w, about 57% w/w, about 58% w/w, about 59% w/w, or about 60% w/w. In another embodiment, the solvent concentration can be about 65% w/w, about 66% w/w, about 67% w/w, about 68% w/w, about 69% w/w, about 70% w/w, about 71% w/w, about 72% w/w, about 73% w/w, about 74% w/w, or about 75% w/w.

In one embodiment, the solvent concentration can be about 57% w/w.

In one embodiment, the solvent concentration can be about 70% w/w.

In one embodiment, the solvent concentration can be about 75% w/w.

In general, monomers can contain moieties such as acrylate, acrylamide, methacrylate, methacrylamide or other moieties amenable to polymerization. In one embodiment, the polymer particles are comprised of one or more macromers combined with one or more monomers.

Optionally, one or more monomers can be added to the polyether macromer to impart desired chemical and/or mechanical properties to the polymer particle. If the binding of positively charged drugs or other materials is desired, monomers with negatively charged moieties, e.g. carboxylic acids, can be polymerized into the particles. Acidic unsaturated monomers can include, but are not limited to, acrylic acid, methacrylic acid, 3-sulfopropyl acrylate, 3-sulfopropyl methacrylate, derivatives thereof, combinations thereof, and salts thereof. If the binding of negatively charged drugs is desired, monomers with positively charged moieties, e.g. amines, can be polymerized into the particles. Basic monomers can include amino ethyl methacrylate, 2-amino ethyl methacrylate, amino propyl methacrylamide, derivatives thereof, combinations thereof, and salts thereof.

Monomers including positive or negative moieties can be present in solution at concentrations of about 0.5% w/w, about 1% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 40% w/w, about 50% w/w, about 55% w/w, about 60% w/w, about 65% w/w, about 70% w/w, about 80% w/w, between about 1% w/w and about 10% w/w, between about 1% w/w and about 5% w/w, between about 15% w/w and about 35% w/w, or between about 20% w/w and about 30% w/w.

In one embodiment, a monomer(s) including charged moieties can be included at a concentration of about 14% w/w in the solution.

In one embodiment, a monomer(s) including charged moieties can be included at a concentration of about 24% w/w in the solution.

In one embodiment, 2-amino ethyl methacrylate can be included at a concentration of about 0.7% w/w in the solution.

In one embodiment, amino propyl methacrylamide can be included at a concentration of about 0.5% w/w in the solution.

In one embodiment, the monomer is not n-isopropyl acrylamide. In other embodiments, the polymer particles described herein do not include n-isopropyl acrylamide.

If desired, uncharged, reactive moieties can be introduced into the particles. For example, hydroxyl groups can be introduced into the particles with the addition of 2-hydroxyethyl acrylate, 2-hydroxyethyl methacrylate, glycerol monomethacrylate, glycerol monoacrylate, sorbitol monomethacrylate, sorbitol monoacrylate, a carbohydrate similar to sorbitol and amenable to polymerization, derivatives thereof, or combinations thereof. Alternatively, uncharged, relatively un-reactive moieties can be introduced into the particles. For example, acrylamide, methacrylamide, methyl methacrylate, derivatives thereof, or combinations thereof can be added to the polyether macromer. In some embodiments, the monomer(s) can be selected to vary the number of hydroxyl groups in the polymeric particles to enable the particles to remain suspended in radiopaque contrast solution used in the preparation of the particle for clinical use.

Such uncharged moieties if included can be present in the final particle (not including solvents, initiators, and salts) at about 0% w/w, about 10% w/w, about 20% w/w, about 30% w/w, about 40% w/w, about 50% w/w, about 60% w/w, about 61% w/w, about 62% w/w, about 63% w/w, about 64% w/w, about 65% w/w, about 66% w/w, about 67% w/w, about 68% w/w, about 69% w/w, about 70% w/w, about 71% w/w, about 72% w/w, about 73% w/w, about 74% w/w, about 75% w/w, about 80% w/w, about 90% w/w, between about 50% w/w and about 90% w/w, between about 60% w/w and about 70% w/w, between about 65% w/w and about 70% w/w, or between about 67% w/w and about 69% w/w.

In one embodiment, an uncharged moiety can be present at about 68% w/w of the final particle.

In one embodiment, the uncharged moiety can be glycerol monomethacrylate.

Adding multifunctional crosslinkers containing more than one moiety amenable to polymerization can create a more cohesive hydrogel polymer by adding crosslinking to the molecular structure. In some embodiments the polymer particles are comprised of a macromer combined with one or more multifunctional crosslinkers such as, but not limited to, glycerol dimethacrylate, glycerol diacrylate, sorbitol dimethacrylate, sorbitol acrylate, a derivatized carbohydrate similar to sorbitol, derivatives thereof, or combinations thereof. In a preferred embodiment the multifunctional crosslinker is N,N'-methylenebisacrylamide.

If used, a crosslinker can be present in the solution used to form the particles at a concentration of about 0.1% w/w, about 0.25% w/w, about 0.5% w/w, about 0.75% w/w, about 1.0% w/w, about 1.25% w/w, about 1.5% w/w, about 1.75% w/w, about 2% w/w, about 3% w/w, about 4% w/w, about 5% w/w, about 6% w/w, about 7% w/w, about 10% w/w, about 20% w/w, about 25% w/w, about 30% w/w, between about 0% w/w and about 10% w/w, between about 0% w/w and about 2% w/w, between about 0.5% w/w and about 1.5% w/w, between about 0.25% w/w and about 1.75% w/w, or between about 0.1% w/w and about 2% w/w.

In one embodiment, a crosslinker is not used.

In one embodiment, a crosslinker can be present at about 1% w/w.

In one embodiment, the crosslinker can be N,N'-methylenebisacrylamide.

Any amounts of macromer(s), monomer(s), and multifunctional crosslinker(s) can be used in the solution used to form the particles that allows for a desired particle. Total concentration of reactive compounds or solids in the solution can be about 5% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 30% w/w, about 31% w/w, about 32% w/w, about 33% w/w, about 34% w/w, about 35% w/w, about 36% w/w, about 37% w/w, about 38% w/w, about 39% w/w, 40% w/w, about 50% w/w, about 60% w/w, about 70% w/w, between about 10% and 60%, between about 15% w/w and about 50% w/w, or between about 20% w/w and about 40% w/w.

In one embodiment, the total concentration of reactive compounds in the solution can be about 20% w/w.

In one embodiment, the total concentration of reactive compounds in the solution can be about 41% w/w.

In one embodiment, polymer particles can be prepared from monomers having a single functional group and/or macromers having two or more functional groups suitable for polymerization. Functional groups can include those suitable to free radical polymerization, such as acrylate, acrylamide, methacrylate, and methacrylamide. Other polymerization schemes can include, but are not limited to nucleophile/N-hydroxysuccinimide esters, nucleophile/halide, vinyl sulfone/acrylate or maleimide/acrylate. Selection of the monomers is governed by the desired chemical and mechanical properties of the resulting particle.

Concentrations of macromers in the final desiccated particle products can be at a concentration of about 10% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 50% w/w, about 60% w/w, about 70% w/w, about 80% w/w, between about 15% w/w and about 60% w/w, between about 20% w/w and about 50% w/w, between about 25% w/w and about 45% w/w, between about 25% w/w and about 40% w/w, between about 35% w/w and about 45% w/w, between about 37% w/w and about 43% w/w, between about 39% w/w and about 41% w/w, between about 25% w/w and about 35% w/w, between about 26% w/w and about 30% w/w, or between about 27% w/w and about 29% w/w.

In one embodiment, the concentration of macromer(s) in the final desiccated particle products can be about 40% w/w.

In one embodiment, the concentration of macromer(s) in the final desiccated particle products can be about 27% w/w.

In one embodiment, poly(ethylene glycol) diacrylamide is present in the final desiccated particle products at about 40% w/w.

In one embodiment, poly(ethylene glycol) diacrylamide is present in the final desiccated particle products at about 27% w/w.

Concentrations of crosslinkers in the final desiccated particle products can be about 0.1% w/w, about 0.25% w/w, about 0.5% w/w, about 0.75% w/w, about 1% w/w, about 1.25% w/w, about 1.5% w/w, about 1.75% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 25% w/w, about 30% w/w, between about 0% w/w and about 5% w/w, between about 0% w/w and about 2% w/w, between about 0.5% w/w and about 1.5% w/w, between about 0.25% w/w and about 1.75% w/w, or between about 0.1% w/w and about 2% w/w.

In one embodiment, a crosslinker can be present in the final desiccated particle products at about 1% w/w.

In one embodiment, no crosslinker can be present in the final desiccated particle products.

In one embodiment, the crosslinker can be N,N'-methylenebisacrylamide.

Concentrations of one or more monomers in the final desiccated products can be about 10% w/w, about 15% w/w, about 20% w/w, about 25% w/w, about 30% w/w, about 40% w/w, about 50% w/w, about 55% w/w, about 60% w/w, about 61% w/w, about 62% w/w, about 63% w/w, about 64% w/w, about 65% w/w, about 66% w/w, about 67% w/w, about 68% w/w, about 69% w/w, about 70% w/w, about 71% w/w, about 72% w/w, about 73% w/w, about 74% w/w, about 75% w/w, about 80% w/w, between about 50% w/w and 80% w/w, between about 60% w/w and 70% w/w, between about 50% w/w and 80% w/w, between about 50% w/w and 75% w/w, between about 55% w/w and about 65% w/w, between about 57% w/w and 63% w/w, between about 59% w/w and 61% w/w, between about 63% w/w and 73% w/w, between about 65% w/w and 71% w/w, or between about 67% w/w and 69% w/w.

In one embodiment, the concentration of one or more monomers in the final desiccated products can be about 72% w/w.

In one embodiment, the concentration of one or more monomers in the final desiccated products can be about 60% w/w.

In one embodiment, the one or more monomers can be glycerol monomethacrylate and 2-amino ethyl methacrylate.

In one embodiment, glycerol monomethacrylate can be present at a concentration of about 68% w/w of the final desiccated products and 2-amino ethyl methacrylate can be present at a concentration of about 3% w/w of the final desiccated products.

In one embodiment, the one or more monomers can be 3-sulfopropyl acrylate and amino propyl methacrylamide.

In one embodiment, 3-sulfopropyl acrylate can be present at a concentration of about 59% w/w of the final desiccated products and amino propyl methacrylate can be present at a concentration of about 1% w/w of the final desiccated products A skilled artisan understands how to calculate final concentrations based on amount in solvent already discussed.

The polymerization of the macromer and optional one or more monomers using free radical polymerization may require one or more initiators to start the reaction. The polymerization solution can be polymerized by reduction-oxidation, radiation, heat, or any other method known in the art. Radiation polymerization of the prepolymer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the prepolymer solution. In one embodiment, the polymerization method utilizes azobisisobutyronitrile (AIBN) or another water soluble AIBN derivative (2,2'-azobis(2-methylpropionamidine) dihydrochloride). Other initiators useful according to the present description include N,N,N',N'-tetramethylethylenediamine, ammonium persulfate, benzoyl peroxides, and combinations thereof, including azobisisobutyronitriles.

In another embodiment, the initiator can be a combination of N,N,N',N'-tetramethylethylenediamine and ammonium persulfate at a concentration of about 0.25% w/w and about 2% w/w, respectively. In another embodiment, an initiator includes a combination of about 1.5% ammonium persulfate and about 0.3% N,N,N',N'-tetramethylethylenediamine. In still another embodiment, an initiator includes a combination of about 1.8% ammonium persulfate and about 0.2% N,N,N',N'-tetramethylethylenediamine.

The polymerization solution can be prepared by dissolving the reactants such as combinations of monomer(s), macromers(s), multifunctional crosslinkers(s), and optionally initiator(s) in a solvent. The particle embolics can be prepared by emulsion polymerization. A non-solvent for the monomer solution, typically mineral oil when the monomer solvent is water, is sonicated to remove any entrapped oxygen. The mineral oil is added to the reaction vessel. An overhead stirrer is placed in the reaction vessel. The reaction vessel is then sealed, degassed under vacuum, and sparged with an inert gas such as argon. The initiator component N,N,N',N'-tetramethylethylenediamine is added to the reaction vessel and stirring commenced. Ammonium persulfate is added to the polymerization solution and both are then added to the reaction vessel, where the stirring suspends droplets of the polymerization solution in the mineral oil. A surfactant can be added before, after, or during the addition of the polymerization solution to stabilize the suspension. The rate of stirring can affect particle size, with faster stirring producing smaller particles. Stirring rates can be about 100 µm, about 200 µm, about 300 µm, about 400 µm, about 500 µm, about 600 µm, about 700 µm, about 800 µm, about 900 µm, about 1,000 µm, about 1,100 µm, about 1,200 µm, about 1,300 µm, between about 200 rpm and about 1,200 µm, between about 400 rpm and about 1,000 µm, at least about 100 µm, at least about 200 µm, at most about 250 µm, at most about 500 µm, at most about 1,000 µm, at most about 1,300 µm, or at most about 1,200 µm to produce particles with desired diameters.

Desired hydrated polymer particle diameters can be about 10 µm, about 20 µm, about 30 µm, about 40 µm, about 50 µm, about 100 µm, about 200 µm, about 300 µm, about 400 µm, about 500 µm, about 600 µm, about 700 µm, about 800 µm, about 900 µm, about 1,000 µm, about 1,100 µm, about 1,200 µm, about 1,300 µm, about 1,400 µm, about 1,500 µm, about 1,600 µm, about 1,700 µm, about 1,800 µm, about 1,900 µm, about 2,000 µm, between about 50 µm and about 1,500 µm, between about 100 µm and about 1,000 µm, at least about 50 µm, at least about 80 µm, less than about 600 µm, less than about 1,000 µm, less than about 1,200 µm, or less than about 1,500 µm. In one embodiment, the diameter is less than about 1,200 µm.

Polymerization can be allowed to proceed as long as necessary to produce particles with desired diameters. Polymerization can be allowed to proceed for about 1 hr, 2 hr, 2.5 hr, 3 hr, 4 hr, 5 hr, 6 hr, 7 hr, 8 hr, 9 hr, 10 hr, 11 hr, 12 hr, 18 hr, 24 hr, 48 hr, 72 hr, 96 hr, between about 1 hr and about 12 hr, between about 1 hr and about 6 hr, between about 4 hr and about 12 hr, between about 6 hr and about 24 hr, between about 12 hr and about 72 hr, or at least about 6 hours.

Polymerization can be run at a temperature to produce particles with desired diameters. Polymerization can be run at a temperature of about 10° C., about 15° C., about 20° C., about 25° C., about 30° C., about 35° C., about 40° C., about 45° C., about 50° C., about 60° C., about 70° C., about 80° C., about 90° C., about 100° C., between about 10° C. and about 100° C., between about 10° C. and about 30° C., at least about 20° C., at most about 100° C., or at about room temperature. In one embodiment, polymerization occurs at room temperature.

After the polymerization is complete, the polymer particles can be washed to remove any solute, mineral oil, un-reacted monomer(s), and/or unbound oligomers. Any solvent may be utilized and can include, but are not limited to hexane, acetone, alcohols, water and a surfactant, water, organic solvents, saline, and combinations thereof. In one embodiment, the washing solution is water. In another embodiment, the washing solution is a combination of hexane followed by water. In another embodiment, the washing solution is saline. In further embodiments, the washing solution is water and a surfactant.

The particles described herein can optionally be loaded or coated with a drug(s) and/or active agent(s) including, but not limited to anti-proliferative compounds, cytostatic compounds, toxic compounds, anti-inflammatory compounds, chemotherapeutic agents, analgesics, antibiotics, protease inhibitors, statins, nucleic acids, polypeptides, growth factors and delivery vectors including recombinant microorganisms, liposomes, and the like. In one embodiment, particles can be loaded with doxorubicin. In another embodiment, the particles can be loaded with irinotecan. In still other embodiments, the particles can be loaded with irinotecan and doxorubicin.

Drugs and/or active agents can be eluted from the particles once implanted. Elution can occur over about 1 hour, about 2 hours, about 5 hours, about 10 hours, about 12 hours, about 18 hours, about 24 hours, about 2 days, about 3 days, about 4 days, about 5 days, about 7 days, about 2 weeks, about 1 month, about 2 months, about 6 months, about 9 months, about 1 year, or about 2 years. For example, about 1 mg, about 2 mg, about 3 mg, about 4 mg, about 5 mg, about 10 mg, about 20 mg, about 30 mg, about 40 mg, or about 50 mg of drug or active agent can be eluted from the particles in a 22 hour or 24 hour period.

Optionally, the washed polymer particles can be dyed prior to, during, or after polymerization to permit visualization before injection into a microcatheter. Any of the dyes from the family of reactive dyes which bond covalently to the particle embolics can be used. Dyes can include, but are not limited to, reactive blue 21, reactive orange 78, reactive yellow 15, reactive blue No. 19, reactive blue No. 4, C.I. reactive red 11, C.I. reactive yellow 86, C.I. reactive blue 163, C.I. reactive red 180, C.I. reactive black 5, C.I. reactive orange 78, C.I. reactive yellow 15, C.I. reactive blue No. 19, C.I. reactive blue 21, any of the color additives. Some color additives are approved for use by the FDA part 73, subpart D. In other embodiments, a dye that can irreversibly bond to the polymer matrix of the particle embolic is utilized.

A dye bath can be made by dissolving sodium carbonate and the desired dye in water. Particle embolics are added to the dye bath and stirred. After the dying process, any unbound dye is removed through washing. After dying and washing, the particles can be packaged into vials or syringes, and sterilized.

The particles described herein can be sterilized without substantially degrading the polymer. After sterilization, at least about 50%, about 60%, about 70%, about 80%, about 90%, about 95% about 99% or about 100% of the polymer can remain intact. In one embodiment, the sterilization method can be autoclaving and can be utilized before administration.

The final polymer particle preparation can be delivered to the site to be embolized via a catheter, microcatheter, needle, or similar delivery device. A radiopaque contrast agent can be thoroughly mixed with the particle preparation in a syringe and injected through a catheter until blood flow is determined to be occluded from the site by interventional imaging techniques.

The particles can remain substantially stable once injected. For example, the polymer particles can remain greater than about 60%, about 70% about 80%, about 90%, about 95%, about 99% or about 100% intact after about 5 days, about 2 weeks, about 1 month, about 2 months, about 6 months, about 9 months, about a year, about 2 years, about 5 years, about 10 years, or about 20 years.

The polymer particles described herein can be compressible yet durable enough not to break apart or fragment. Substantially no change in circularity or diameter of particles may occur during delivery through a microcatheter. In other words, after delivery through a microcatheter, the polymer particles described herein remain greater than about 60%, about 70% about 80%, about 90%, about 95%, about 99% or about 100% intact.

In one embodiment, particles before delivery through a microcatheter can have an average diameter of 0.221±0.054 mm and a post-delivery diameter of 0.226±0.049 mm. These particles can also exhibit a pre-delivery average formcircle of 0.98±0.04 and a post-delivery formcircle of 0.98±0.02.

In another embodiment, particles before delivery through a microcatheter can have an average diameter of 395±25 μm and a post-delivery diameter of 401±30 μm. These particles can also exhibit a pre-delivery average formcircle of 0.98±0.01 and a post-delivery formcircle of 0.98±0.04.

Further, the particles can be cohesive enough to stick to tissue and/or remain in place through friction with the tissue. In other embodiments, the particles can act as a plug in a vessel held in place by the flow and pressure of blood.

In one example embodiment, a polymer particle can include a reaction product of a polyether, glycerol monomethacrylate, bisacrylamide, and aminoethyl methacrylate. In another example embodiment, a desiccated polymer particle can include a polyether at about 28% w/w, glycerol monomethacrylate at about 68% w/w, bisacrylamide at about 1% w/w, and aminoethyl methacrylate at about 3% w/w.

On another example embodiment, a dessicated polymer particle can include a reaction product of a polyether, aminopropyl methacrylamide, and sulfopropyl acrylate. In another embodiment, a polymer particle can include a polyether at about 40%, aminopropyl methacrylamide at about 1%, and sulfopropyl acrylate at about 59%.

Example 1

Preparation of a Polyether Macromer

Polyethylene glycol 10,000 (450 g) was dried by azeotropic distillation with 2,400 mL of toluene. Then, 200 mL of dichloromethane, 15.6 mL of triethylamine, and 10.4 mL of mesyl chloride were added and the solution was stirred for 4 hr. The solution was filtered, the product precipitated in diethyl ether, and collected by filtration. The resulting product was vacuum dried, added to 3,600 mL of 25% of ammonium hydroxide, and stirred closed for 4 days then open for 3 days. The water was removed and the product dried by azeotropic distillation with toluene. To the resulting poly(ethylene glycol) diamine in toluene, 15.6 mL of triethylamine and 10.9 mL of acryloyl chloride were added and the reaction was stirred for 4 hr. The resulting solution was filtered, precipitated in ether and the solvent removed, yielding PEG 10,000 diacrylamide.

Example 2

Particle Embolic Prepared with a Polyether Macromer and a Plurality of Monomers

The prepolymer formulation is prepared by dissolving 0.25 g 2-aminoethyl methacrylate, 2.125 g poly(ethylene glycol) diacrylamide from Example 1, 5.1 g glycerol monomethacrylate, 0.07 g N,N'-methylenebisacrylamide, and 1.2 g sodium chloride in 20 mL of de-ionized water. The solution was filtered into a clean 120 mL amber jar. An initiator solution was made by dissolving 1.0 g ammonium persulfate in 2.0 g of de-ionized water. Then, 1.0 mL of the ammonium persulfate solution was added to the filtered prepolymer solution, and the solution was vacuum degassed for 2 min, and the vacuum was replaced with argon. 500 mL of mineral oil were sonicated for 1 hr, and then added to a sealed reaction vessel with an overhead stirring element. The vessel was vacuum degassed for 1 hr, and then the vacuum replaced with argon. Then, 1 mL of N,N,N',N'-tetramethylethylenediamine was added to the reaction vessel and overhead stirring started at 200 rpm. The prepolymer formulation was added to the reaction vessel. After 1 min, 0.1 mL of SPAN® 80 (sorbitan monooleate, Croda International Plc, East Yorkshire, purchased from Sigma-Aldrich Company LLC, St. Louis, Mo.) was added and the preparation was allowed to polymerize for at least 2 hr. The oil was decanted off and the particles were poured into a seperatory funnel with 1,000 mL of de-ionized water. The bottom water/sphere layer was collected. The particles were washed with several 300 mL portions of hexane. After the final wash, all hexane was decanted off and the particles were washed several times with fresh 300 mL portions of de-ionized water and stored in a capped bottle with de-ionized water.

Example 3

Particle Embolic Prepared with a Polyether Macromer

A prepolymer formulation was prepared by dissolving 15.8 g poly(ethylene glycol) diacrylamide and 6.0 g of sodium chloride in 30.0 g of de-ionized water. Then, 10 g of this solution was filtered. An initiator solution was made by dissolving 1.0 g ammonium persulfate in 2.0 grams of de-ionized water. The ammonium persulfate solution (1 mL) was added to the filtered prepolymer solution, the solution was vacuum degassed for 2 min, and the vacuum was replaced with argon. Then, 500 mL of mineral oil was sonicated for 2 hr, and then added to a sealed reaction vessel with 0.5 mL of SPAN® 80 and an overhead stirring element. The vessel was vacuum degassed for 1 hr, and then the vacuum replaced with argon. Then, 1 mL of N,N,N',N'-tetramethylethylenediamine was added to the reaction vessel and overhead stirring started at 450 rpm. The 10 g of prepolymer formulation was added to the reaction vessel via syringe and allowed to polymerize for at least 8 hr.

Example 4

Particle Embolic Prepared with a Polyether Macromer and Monomer

A prepolymer formulation was prepared by dissolving 9.2 g poly(ethylene glycol) diacrylamide from Example 1, 13.8 g 3-sulfopropyl acrylate potassium salt, and 0.248 g n-(3-aminopropyl)methacrylamide hydrochloride in 34.4 g of deionized water. Then, the solution was filtered. An initiator solution was made by dissolving 1.0 g ammonium persulfate in 2.0 g of deionized water. Ammonium persulfate solution (0.85 mL) was added to the filtered prepolymer solution, the solution was then vacuum degassed for 2 min, and added to a sealed reaction vessel with 0.14 mL of SPAN® 80 and an overhead stirring element. The vessel was vacuum degassed for 1 hr, and then the vacuum was replaced with argon. N,N,N'N'-tetramethylethylenediamine (2 mL) was added to the reaction vessel and overhead stirring started at 400 rpm. The prepolymer formulation was added to the reaction vessel via syringe and allowed to polymerize for at least 8 hr.

Example 5

Purification of Particle Embolics

The mineral oil was decanted from the reaction vessel, and the polymer particles were washed three times with fresh portions of hexane to remove the mineral oil. The particles were then transferred to a separatory funnel with water, and separated from residual mineral oil and hexane. Next, the particles are washed with de-ionized water to remove any residual reactants. The particles can be packaged in 0.9% saline solution for the final preparation or dyed.

Example 6

Dying of Particle Embolics

To dye the particles, 50 g of sodium carbonate and 0.1 g reactive black 5 dye (Sigma-Aldrich Co. LLC, St. Louis, Mo.) were dissolved in 1,000 mL of de-ionized water. Then, 500 mL of drained particles were added and allowed to stir for 1 hr. The dyed particle preparation was washed with de-ionized water until all residual dye was removed. The particles can then be packaged in 0.9% saline solution for the final preparation.

Example 7

Drug Loading Particle Embolics

Particles prepared in Example 4 were sieved to 100-300 µm and loaded with the drug doxorubicin. Four 1 mL particle aliquots were loaded with 37.5 mg of doxorubicin in solution. The solution was analyzed by an Agilent 1100 HPLC system before and after adding particles to determine amount of drug sequestered by the particles from the solution.

Loading particles with doxorubicin: 37.5 mg of doxorubicin was dissolved in 2 mL of deionized water. A drop of the drug solution was saved for LC analysis. The saline storage fluid was removed from a 1 mL vial of particles and the drug solution added to the vial of particles. After 18 hours, a sample of the solution was analyzed, and the drug loading was determined by comparing peak area of drug present in solution before and after adding particles.

Particles prepared in Example 4 were similarly loaded with the drug irinotecan. Four 1 mL aliquots of particles sized 100-300 µm were loaded with 50.0 mg of irinotecan dissolved in citrate buffer solution. The solution was analyzed before and after adding particles.

Figure 1:
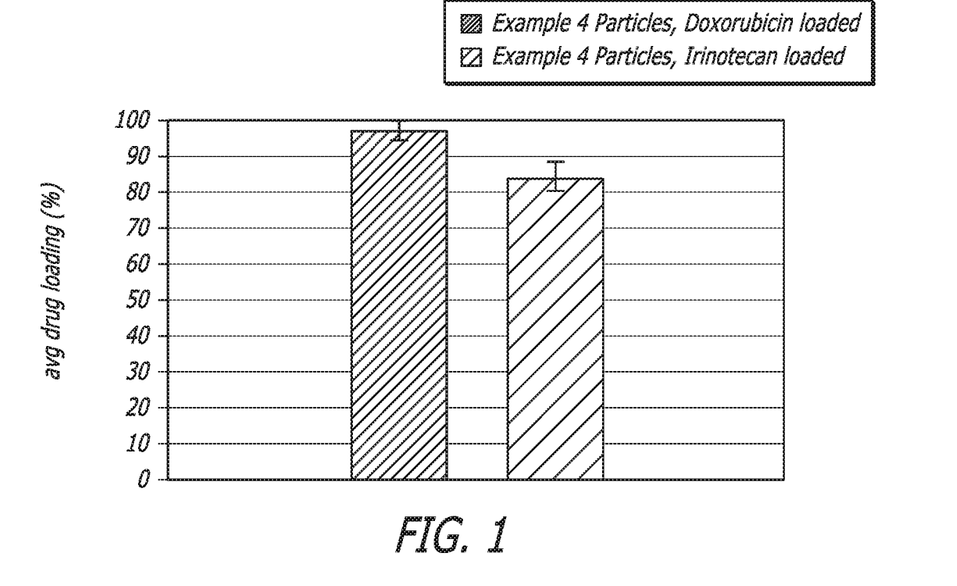
FIG. 1 illustrates a plot of average drug loading of particles charged with doxorubicin or irinotecan.

Loading particles with irinotecan: 50.0 mg of irinotecan was dissolved in 5 mL of pH 4 citrate buffer solution. A drop of the solution was saved for LC analysis. The saline storage solution was removed from a 1 mL vial of particles and the irinotecan solution was added. After 18 hr a sample of the solution was analyzed and the drug loaded determined by comparing the peak area of drug present in solution before and after adding particles (FIG. 1).

Example 8

Drug Elution of Particle Embolic

Particles prepared in example 4 were aliquoted into six 1 mL samples and loaded with drug per Example 7. Excess drug solution was removed from the sample of particles after an 18 hr incubation period. The samples were placed into the dissolution chambers of a Sotax CE7 Smart USP 4 dissolution apparatus. The elution media of saline solution was run at 37.5° C. for 22 hours with samples taken at various time points. The samples were analyzed by an Agilent 1100

13

Figure 2:
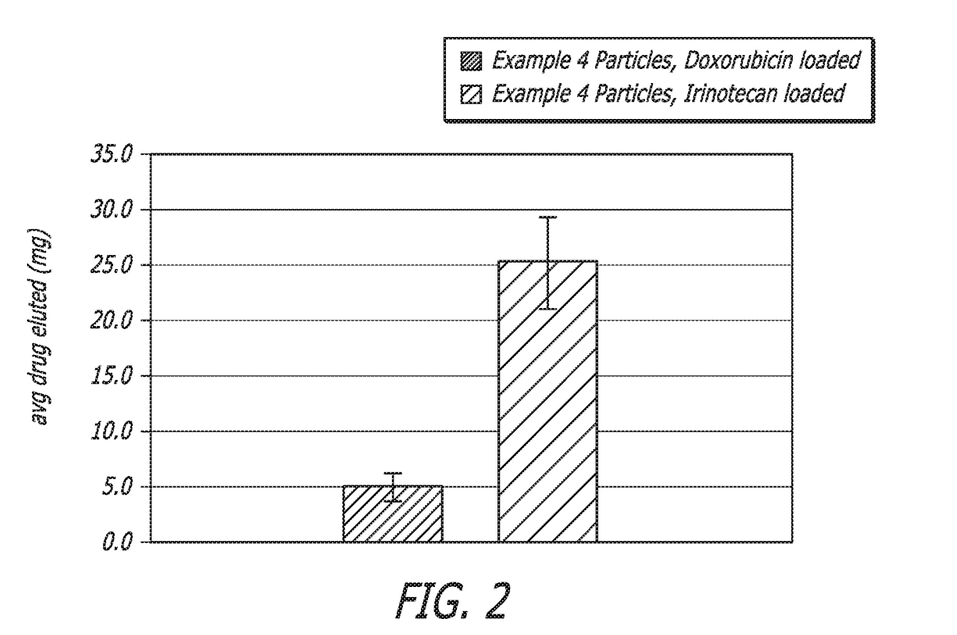
FIG. 2 illustrates a plot of average drug elution from particles at 22 hours after in situ.

HPLC system and milligrams of drug eluted calculated. Results are illustrated in FIG. 2.

Example 9

Compressive Modulus of Particle Embolic

Particles created as described herein are often delivered through a catheter with a smaller inner lumen than the average outer diameter of the particles. The compressive modulus required to compress a sample of particles to 30% of their a nominal diameter was tested on a Instron 5543 materials testing machine equipped with a 5 N load cell. To test a sample, an approximately 1 cm circular monolayer of spherical particles stored in saline, nominally sized 800 µm diameter, was placed on a flat lower platen. Excess saline was carefully blotted away with a lab wipe. A flat probe compressed the beads to 30% of the beads' average diameter and the Young's modulus was recorded. The test was repeated 3-5 times for each sample.

Figure 3:
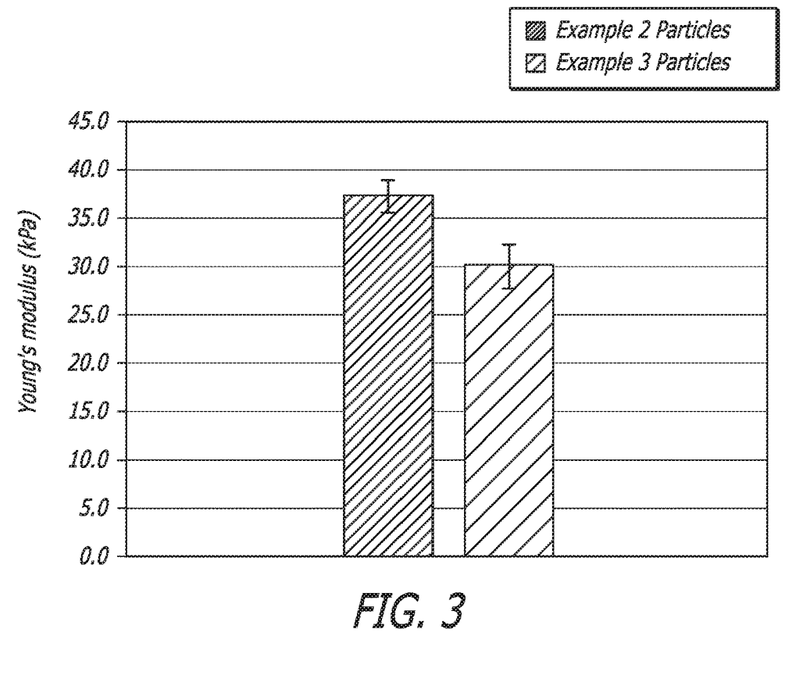
FIG. 3 illustrates a plot of particle compressibility at 30% deformation.

Two samples of spherical particles nominally sized 800 µm diameter from Example 2 and Example 3 were tested as described previously and the results are illustrated in FIG. 3.

Figure 4:
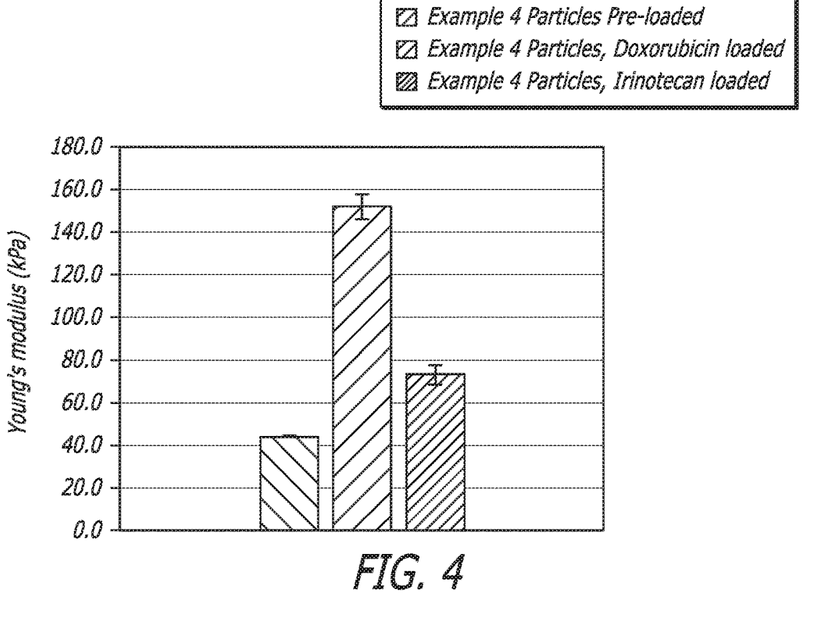
FIG. 4 illustrates another plot of particle compressibility at 30% deformation.

Two 1 mL aliquots of spherical particles nominally sized 800 µm from Example 4 were loaded with irinotecan and doxorubicin per Example 7. The compressibility was measured before and after loading with drug and the results are illustrated in FIG. 4.

Example 10

Determination of Suspension Properties of Particles in Radiopaque Contrast

Particle embolics can be prepared for delivery in radiopaque contrast solution. A homogeneous mixture of particles suspended in contrast solution can permit a uniform injection of beads through a catheter. To test suspension characteristics of embolic particles, a 10 mL syringe with 1 mL of particles and 2 mL of buffered saline were attached to a 3-way stopcock. Another syringe containing 3 mL of OMNIPAQUE® 300 (iohexol formulated as 300 mg of iodine per mL, GE Healthcare, Norway) contrast was attached to the stopcock. The contrast was injected into the particle syringe and a timer was started. The syringe containing contrast, saline, and particles was removed from the stopcock and capped with a syringe tip cap. The contents were mixed by inverting the syringe repeatedly. At a time point, the mixing was stopped and a second timer started. The time taken for particles to remain only in ⅔ of the syringe was recorded. Mixing by inverting was continued between measurements.

Figure 5:
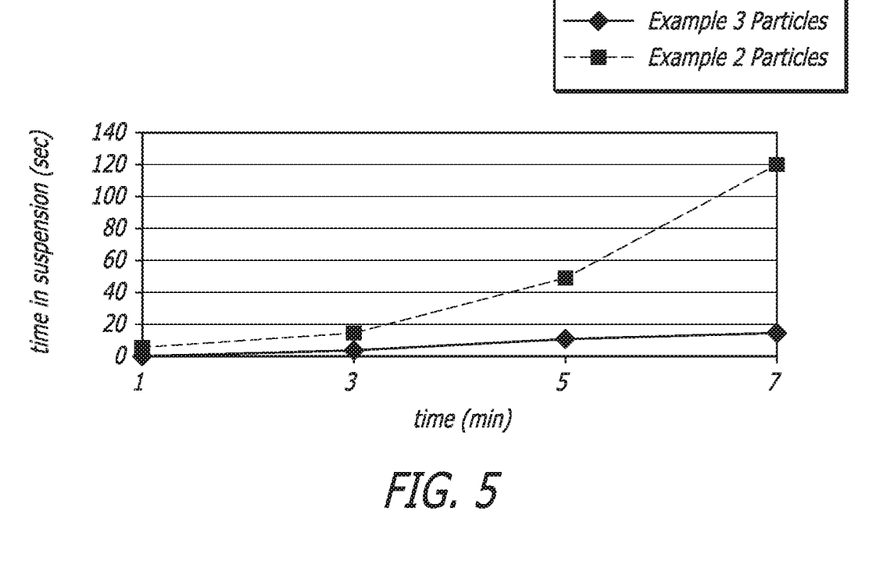
FIG. 5 illustrates a plot of particle time in suspension.

Particles from Example 2 and Example 3, nominally sized 800 µm diameter were tested using the method described above and results are illustrated in FIG. 5.

Particles from Example 4, nominally sized 400 µm and drug loaded with doxorubicin were tested for suspension characteristics. To do so, 1 mL of the drug loaded particles and the solution they were drug loaded in were placed in a 10 mL syringe. Excess drug solution was expressed from the syringe and the syringe was attached to a 3-way stop cock. A second 10 mL syringe containing OMNIPAQUE® 300 contrast was attached to the 3-way stopcock. Enough contrast solution was added to the syringe containing the particles to make a total volume of 6 mL and the timer was started. The syringe containing contrast and particles was removed from the stopcock and capped with a syringe tip cap. The contents were mixed by inverting the syringe repeatedly. At a time point, the mixing was stopped and a second timer started. The time taken for particles to remain only in ⅔ of the syringe was recorded. Mixing by inverting was continued between measurements.

Particles from Example 4, nominally sized 400 µm and drug loaded with irinotecan were tested for suspension characteristics. To do so, 1 mL of the drug loaded particles and drug loading solution were placed in a 10 mL syringe. Excess drug solution was expressed from the syringe and the syringe was attached to a 3-way stopcock. A second 10 mL syringe containing de-ionized water was attached to the 3-way stopcock and water was injected into the syringe containing the drug loaded particles to bring the total volume to 3 mL. The syringe containing water was removed and a syringe containing OMNIPAQUE® 300 contrast was attached to the 3-way stopcock. Enough contrast solution was added to the syringe containing the particles to make a total volume of 6 mL and the timer was started. The syringe containing contrast and particles was removed from the stopcock and capped with a syringe tip cap. The contents were mixed by inverting the syringe repeatedly. At various time points, the mixing was stopped and a second timer started. The time taken for particles to remain only in ⅔ of the syringe was recorded. Mixing by inverting was continued between measurements.

Figure 6:
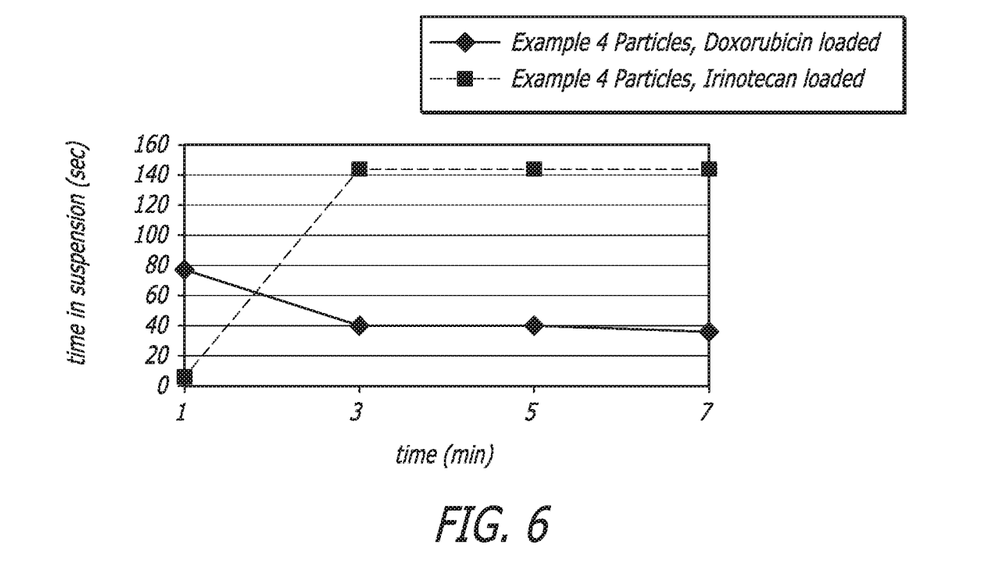
FIG. 6 illustrates a plot of drug loaded particle time in suspension.

Results for particles loaded with doxorubicin and irinotecan are illustrated in FIG. 6.

Example 11

Determination of Durability of Particle Embolics after Catheter Delivery

To simulate use, a 1 mL sample of particles prepared in Example 3 was injected through a Headway 21 catheter (0.021", 533 µm inner lumen). One milliliter of particles with 2 mL of saline in a syringe were attached to a 3-way stopcock. The catheter and a syringe containing 3 mL of OMNIPAQUE® 300 contrast solution were also attached to the 3-way stopcock. The stopcock was opened between the syringes to mix the beads, saline, and contrast. This particle preparation was then contained in one syringe, the other syringe removed, and a 1 mL injection syringe attached to the stopcock in line with the catheter. The particles were delivered through the catheter into a dish. An image was acquired using a Zeiss Axio Imager A1 microscope and analyzed using Zeiss Axiovision image analysis software. The circularity (closeness to a circle) was scored and statistical analysis using a Student's t-test indicated no difference in the spherical particles before and after delivery, with no damaged spheres observed.

| Pre-Delivery Table | | |
|---|---|---|
| Sphere # | Formcircle | Diameter (µm) |
| 1 | 0.93 | 481 |
| 2 | 0.97 | 372 |
| 3 | 0.97 | 411 |
| 4 | 0.97 | 390 |
| 5 | 0.97 | 373 |
| 6 | 0.97 | 407 |
| 7 | 0.97 | 405 |
| 8 | 0.97 | 388 |
| 9 | 0.98 | 412 |
| 10 | 0.98 | 393 |

Pre-Delivery Table

| Sphere # | Formcircle | Diameter (μm) |
|---|---|---|
| 11 | 0.98 | 414 |
| 12 | 0.98 | 388 |
| 13 | 0.98 | 386 |
| 14 | 0.98 | 360 |
| 15 | 0.98 | 433 |
| 16 | 0.98 | 380 |
| 17 | 0.98 | 414 |
| 18 | 0.98 | 404 |
| 19 | 0.98 | 361 |
| 20 | 0.98 | 385 |
| 21 | 0.98 | 376 |
| 22 | 0.98 | 387 |
| 23 | 0.98 | 373 |
| 24 | 0.98 | 376 |
| 25 | 0.98 | 396 |
| 26 | 0.98 | 443 |
| 27 | 0.98 | 380 |
| 28 | 0.98 | 380 |
| 29 | 0.99 | 412 |
| 30 | 0.99 | 381 |

Post-Delivery Table

| Sphere # | Formcircle | Diameter (μm) |
|---|---|---|
| 1 | 0.7 | 564 |
| 2 | 0.83 | 432 |
| 3 | 0.85 | 458 |
| 4 | 0.91 | 455 |
| 5 | 0.92 | 411 |
| 6 | 0.93 | 375 |
| 7 | 0.94 | 475 |
| 8 | 0.95 | 463 |
| 9 | 0.96 | 414 |
| 10 | 0.97 | 391 |
| 11 | 0.97 | 388 |
| 12 | 0.97 | 391 |
| 13 | 0.97 | 397 |
| 14 | 0.97 | 376 |
| 15 | 0.98 | 395 |
| 16 | 0.98 | 378 |
| 17 | 0.98 | 400 |
| 18 | 0.98 | 359 |
| 19 | 0.98 | 380 |
| 20 | 0.98 | 381 |
| 21 | 0.98 | 416 |
| 22 | 0.98 | 412 |
| 23 | 0.98 | 410 |
| 24 | 0.98 | 418 |
| 25 | 0.98 | 382 |
| 26 | 0.98 | 404 |
| 27 | 0.98 | 409 |
| 28 | 0.98 | 411 |
| 29 | 0.98 | 387 |
| 30 | 0.98 | 376 |
| 31 | 0.98 | 416 |
| 32 | 0.98 | 426 |
| 33 | 0.99 | 392 |
| 34 | 0.99 | 424 |
| 35 | 0.99 | 388 |
| 36 | 0.99 | 390 |
| 37 | 0.99 | 390 |
| 38 | 0.99 | 391 |
| 39 | 0.99 | 385 |
| 40 | 0.99 | 386 |
| 41 | 0.99 | 417 |
| 42 | 0.99 | 411 |
| 43 | 0.99 | 398 |
| 44 | 0.99 | 439 |
| 45 | 0.99 | 419 |
| 46 | 0.99 | 386 |
| 47 | 0.99 | 418 |
| 48 | 0.99 | 368 |
| 49 | 0.99 | 420 |
| 50 | 0.99 | 375 |
| 51 | 0.99 | 391 |
| 52 | 0.99 | 392 |
| 53 | 0.99 | 418 |
| 54 | 0.99 | 384 |
| 55 | 0.99 | 369 |
| 56 | 0.99 | 396 |
| 57 | 0.99 | 408 |
| 58 | 1 | 399 |
| 59 | 1 | 387 |
| 60 | 1 | 395 |
| 61 | 1 | 391 |
| 62 | 1 | 388 |
| 63 | 1 | 391 |
| 64 | 1 | 370 |
| 65 | 1 | 409 |
| 66 | 1 | 364 |
| 67 | 1 | 392 |
| 68 | 1 | 364 |
| 69 | 1 | 415 |
| 70 | 1 | 371 |
| 71 | 1 | 423 |
| 72 | 1 | 380 |
| 73 | 1 | 406 |
| 74 | 1 | 428 |
| 75 | 1 | 364 |
| 76 | 1 | 367 |
| 77 | 1 | 371 |
| 78 | 1 | 381 |
| 79 | 1 | 384 |
| 80 | 1 | 389 |
| 81 | 1 | 408 |

Summary Table

| | |
|---|---|
| Average Diameter Pre-delivery, μm | 395 ± 25 |
| Average Diameter Post-delivery, μm | 401 ± 30 |
| Average Formcircle Pre-delivery | 0.98 ± 0.01 |
| Average Formcircle Post-delivery | 0.98 ± 0.04 |

Example 12

Determination of Durability of Drug Loaded Particle Embolics After Delivery

To simulate use of a drug loaded particle embolic, 1 mL sample of particles prepared in Example 4 was injected through a Headway 17 catheter (0.017", 432 μm inner lumen). Then, a syringe charged with 1 mL of particles loaded with doxorubicin per example 7 with 2 mL of de-ionized water was attached to a 3-way stopcock. The catheter and a syringe containing 3 mL of OMNIPAQUE® 300 radiopaque contrast solution were also attached to the 3-way stopcock. The stopcock was opened between the syringes to mix the beads, saline, and contrast. This particle preparation was then contained in one syringe, the other syringe removed, and a 1 mL injection syringe attached to the stopcock in line with the catheter. The particles were delivered through the catheter into a dish. An image was acquired using a Zeiss Axio Imager A1 microscope and analyzed using Zeiss Axiovision image analysis software. The circularity (closeness to circle) was scored and statistical analysis using a Student's t-test indicated no difference in the spherical particles before and after delivery, with no damaged spheres observed.

Pre-Delivery Table

| Sphere # | Formcircle | Diameter (mm) |
|---|---|---|
| 1 | 0.73 | 0.173 |
| 2 | 0.95 | 0.148 |
| 3 | 0.95 | 0.266 |
| 4 | 0.96 | 0.265 |
| 5 | 0.96 | 0.203 |
| 6 | 0.96 | 0.159 |
| 7 | 0.97 | 0.221 |
| 8 | 0.97 | 0.263 |
| 9 | 0.97 | 0.176 |
| 10 | 0.98 | 0.305 |
| 11 | 0.98 | 0.2 |
| 12 | 0.98 | 0.172 |
| 13 | 0.98 | 0.193 |
| 14 | 0.98 | 0.237 |
| 15 | 0.98 | 0.226 |
| 16 | 0.98 | 0.202 |
| 17 | 0.98 | 0.277 |
| 18 | 0.98 | 0.203 |
| 19 | 0.98 | 0.288 |
| 20 | 0.99 | 0.167 |
| 21 | 0.99 | 0.213 |
| 22 | 0.99 | 0.176 |
| 23 | 0.99 | 0.203 |
| 24 | 0.99 | 0.301 |
| 25 | 0.99 | 0.27 |
| 26 | 0.99 | 0.199 |
| 27 | 0.99 | 0.247 |
| 28 | 0.99 | 0.208 |
| 29 | 0.99 | 0.212 |
| 30 | 0.99 | 0.391 |
| 31 | 0.99 | 0.201 |
| 32 | 0.99 | 0.177 |
| 33 | 0.99 | 0.175 |
| 34 | 0.99 | 0.158 |
| 35 | 1 | 0.243 |
| 36 | 1 | 0.198 |
| 37 | 1 | 0.299 |
| 38 | 1 | 0.147 |
| 39 | 1 | 0.19 |
| 40 | 1 | 0.189 |
| 41 | 1 | 0.324 |

Post-Delivery Table

| Sphere # | Formcircle | Diameter (mm) |
|---|---|---|
| 1 | 0.89 | 0.252 |
| 2 | 0.93 | 0.211 |
| 3 | 0.94 | 0.176 |
| 4 | 0.94 | 0.26 |
| 5 | 0.95 | 0.208 |
| 6 | 0.95 | 0.298 |
| 7 | 0.95 | 0.23 |
| 8 | 0.96 | 0.233 |
| 9 | 0.96 | 0.186 |
| 10 | 0.97 | 0.274 |
| 11 | 0.97 | 0.142 |
| 12 | 0.97 | 0.302 |
| 13 | 0.97 | 0.211 |
| 14 | 0.97 | 0.247 |
| 15 | 0.97 | 0.271 |
| 16 | 0.97 | 0.236 |
| 17 | 0.97 | 0.173 |
| 18 | 0.97 | 0.267 |
| 19 | 0.98 | 0.266 |
| 20 | 0.98 | 0.233 |
| 21 | 0.98 | 0.214 |
| 22 | 0.98 | 0.174 |
| 23 | 0.98 | 0.244 |
| 24 | 0.98 | 0.212 |
| 25 | 0.98 | 0.273 |
| 26 | 0.98 | 0.288 |
| 27 | 0.98 | 0.275 |
| 28 | 0.98 | 0.258 |
| 29 | 0.98 | 0.27 |
| 30 | 0.98 | 0.191 |
| 31 | 0.98 | 0.191 |
| 32 | 0.98 | 0.214 |
| 33 | 0.98 | 0.26 |
| 34 | 0.98 | 0.173 |
| 35 | 0.98 | 0.224 |
| 36 | 0.98 | 0.13 |
| 37 | 0.98 | 0.266 |
| 38 | 0.98 | 0.34 |
| 39 | 0.98 | 0.221 |
| 40 | 0.98 | 0.134 |
| 41 | 0.99 | 0.212 |
| 42 | 0.99 | 0.291 |
| 43 | 0.99 | 0.298 |
| 44 | 0.99 | 0.206 |
| 45 | 0.99 | 0.315 |
| 46 | 0.99 | 0.242 |
| 47 | 0.99 | 0.198 |
| 48 | 0.99 | 0.3 |
| 49 | 0.99 | 0.26 |
| 50 | 0.99 | 0.187 |
| 51 | 0.99 | 0.132 |
| 52 | 0.99 | 0.199 |
| 53 | 0.99 | 0.168 |
| 54 | 0.99 | 0.274 |
| 55 | 0.99 | 0.186 |
| 56 | 0.99 | 0.279 |
| 57 | 0.99 | 0.22 |
| 58 | 0.99 | 0.232 |
| 59 | 0.99 | 0.247 |
| 60 | 0.99 | 0.162 |
| 61 | 0.99 | 0.178 |
| 62 | 0.99 | 0.209 |
| 63 | 1 | 0.147 |
| 64 | 1 | 0.156 |
| 65 | 1 | 0.185 |
| 66 | 1 | 0.204 |

Summary Table

| | |
|---|---|
| Average Diameter Pre-delivery, mm | 0.221 ± 0.054 |
| Average Diameter Post-delivery, mm | 0.226 ± 0.049 |
| Average Formcircle Pre-delivery | 0.98 ± 0.04 |
| Average Formcircle Post-delivery | 0.98 ± 0.02 |

Example 13

Polymer Microsphere Comprised of a Macromer and Plurality of Monomers, Diluted Prepolymer Solution The prepolymer formulation was prepared by dissolving 0.35 g 2-aminoethyl methacrylate, 2.98 g poly(ethylene glycol) diacrylamide from Example 1, 7.16 g glycerol monomethacrylate, 0.098 g N,N'-methylenebisacrylamide, and 3.0 g sodium chloride in 40 mL of de-ionized water. The solution was filtered into a clean 120 mL amber jar. An initiator solution was made by dissolving 1.0 g ammonium persulfate in 2.0 g of de-ionized water. 1.0 mL of the ammonium persulfate solution was added to the filtered prepolymer solution, and the solution was vacuum degassed for 2 min, and the vacuum was replaced with argon. Then, 500 mL of mineral oil were sonicated for 1 hr, and then added to a sealed reaction vessel with an overhead stirring element. The vessel was vacuum degassed for 1 hr, and then the vacuum replaced with argon. Then, 1 mL of N,N,N',N'-tetramethylethylenediamine was added to the reaction vessel and overhead stirring started at 200 rpm. The prepolymer formulation was added to the reaction vessel. After 1 min, 0.1 mL of SPAN® 80 was added and the preparation was allowed to polymerize for at least 2 hr. The oil was decanted off and the particles were poured into a separatory funnel with 1,000 mL of de-ionized water. The bottom water/sphere layer was collected. The particles were washed with several 300 mL portions of hexane. After the final wash, all hexane was decanted off and the particles were washed several times with fresh 300 mL portions of de-ionized water and stored in a capped bottle with de-ionized water.

Example 14

Particle Embolic Prepared with a Polyether Macromer and Monomer

A prepolymer formulation was prepared by dissolving 10.0 g poly(ethylene glycol) diacrylamide from Example 1, and 15.0 g 3-sulfopropyl acrylate potassium salt, in 35.0 g of de-ionized water. Then, 55 g of this solution was filtered. An initiator solution was made by dissolving 1.0 g ammonium persulfate in 2.0 g of deionized water. Ammonium persulfate solution (1 mL) was added to the filtered prepolymer solution, the solution was then vacuum degassed for 2 min, and the vacuum was replaced with argon. Then, 1000 mL of mineral oil was sonicated for 2 hr, and then added to a sealed reaction vessel with 0.5 mL of SPAN® 80 and an overhead stirring element. The vessel was vacuum degassed for 1 hr, and then the vacuum was replaced with argon. N,N,N',N'-tetramethylethylenediamine (1 mL) was added to the reaction vessel and overhead stirring started at 450 rpm. The prepolymer formulation (55 g) was added to the reaction vessel via syringe, then 0.35 mL of SPAN® 80. The beads were allowed to polymerize for at least 8 hr.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A polymer particle comprising:
poly(ethylene glycol) diacrylamide, glycerol monomethacrylate, and amino ethyl methacrylate;
wherein the polymer particle is spherical and has a diameter less than about 1,200 μm.

2. The polymer particle of claim 1, wherein the polymer particle has a diameter between about 40 μm and about 1,200 μm.

3. The polymer particle of claim 1, further comprising N,N-methylenebisacrylamide.

4. The polymer particle of claim 1, wherein the N,N-methylenebisacrylamide is at a concentration of about 1% w/w.

5. The polymer particle of claim 1, wherein the poly(ethylene glycol) diacrylamide is at a concentration of about 28% w/w.

6. The polymer particle of claim 1, wherein the glycerol monomethacrylate is present at a concentration of about 68% w/w.

7. The polymer particle of claim 1, wherein the amino ethyl methacrylate at a concentration of about 3% w/w.

8. The polymer particle of claim 1, wherein the poly(ethylene glycol) diacrylamide is poly(ethylene glycol) diacrylamide 10,000.

9. The particle of claim 1, further comprising a drug.

10. A polymer particle comprising:
poly(ethylene glycol) diacrylamide, 3-sulfopropyl acrylate, and amino propyl methacrylamide,
wherein the polymer particle is spherical and has a diameter less than about 1,200 μm.

11. The polymer particle of claim 10, wherein the polymer particle has a diameter between about 40 μm and about 1,200 μm.

12. The polymer particle of claim 10, wherein the poly(ethylene glycol) diacrylamide is at a concentration of about 40% w/w.

13. The polymer particle of claim 10, wherein the at least one monomer is 3-sulfopropyl acrylate at a concentration of about 59% w/w.

14. The polymer particle of claim 10, wherein the amino propyl methacrylamide is at a concentration of about 1% w/w.

15. The polymer particle of claim 10, wherein the poly(ethylene glycol) diacrylamide is poly(ethylene glycol) diacrylamide 10,000.

16. The particle of claim 11, further comprising a drug.

17. A kit comprising:
a plurality of polymer particles in a container,
wherein the plurality of polymer particles comprise poly(ethylene glycol) diacrylamide, glycerol monomethacrylate, and amino ethyl methacrylate;
wherein the plurality of polymer particles are spherical and have a diameter less than about 1,200 μm.

18. The kit of claim 17, wherein the container is a vial or a syringe.

19. A kit comprising:
a plurality of polymer particles in a container,
wherein the plurality of polymer particles comprise poly(ethylene glycol) diacrylamide, 3-sulfopropyl acrylate, and amino propyl methacrylamide;
wherein the plurality of polymer particles are spherical and have a diameter less than about 1,200 μm.

20. The kit of claim 19, wherein the container is a vial or a syringe.

* * * * *